(12) United States Patent
Lui et al.

(10) Patent No.: US 6,229,017 B1
(45) Date of Patent: May 8, 2001

(54) PROCESS FOR PREPARING QUINOLONE- AND NAPHTHYRIDONE- CARBOXYLIC ACIDS AND ESTERS THEREOF

(75) Inventors: Norbert Lui, Köln; Hans Panskus, Leverkusen; Herbert Müller, Kreuzau-Bilstein, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/330,532

(22) Filed: Jun. 11, 1999

(30) Foreign Application Priority Data

Jun. 12, 1998 (DE) .............................. 198 26 050

(51) Int. Cl.⁷ ..................... C07D 471/02; C07D 215/16; C07D 215/20
(52) U.S. Cl. ........................... 546/123; 546/153; 546/156
(58) Field of Search .................... 546/153, 123, 546/156

(56) References Cited

U.S. PATENT DOCUMENTS 4,699,992  10/1987  Grohe .................................. 558/405

FOREIGN PATENT DOCUMENTS

AU-B-19024/88  10/1990  (AU) .
1337715  12/1994  (CA) .
WO 97/31001  8/1997  (WO) .

OTHER PUBLICATIONS

Patent Abstracts of Japan, vol. 17, No. 361 (C–1080), Jul. 8, 1993, & JP 05 051365 A (Ube Ind Ltd), Mar. 2, 1993 *Zusammenfassung*.

Liebigs Ann. Chem. (month unavailable) 1987, pp. 29–37, Grohe (author).

*Primary Examiner*—D. Margaret Seaman
(74) *Attorney, Agent, or Firm*—Joseph C. Gil; Diderico van Eyl

(57) ABSTRACT

An improved process for preparing quinolone- and naphthyridonecarboxylic acids and esters thereof from benzoyl chlorides and nicotinoyl chlorides, respectively, in which the reaction carried out in the presence of a non-polar to slightly polar solvent without separation of intermediaries that form during the process.

15 Claims, No Drawings

PROCESS FOR PREPARING QUINOLONE- AND NAPHTHYRIDONE- CARBOXYLIC ACIDS AND ESTERS THEREOF

FIELD OF THE INVENTION

The invention relates to an improved process for preparing quinolone- and naphthyridonecarboxylic acids and esters thereof starting from benzoyl chlorides and nicotinoyl chlorides, respectively.

BACKGROUND OF THE INVENTION

Quinolone- and naphthyridonecarboxylic acids and esters thereof are intermediates for preparing known, pharmaceutically active quinolone-carboxylic acids and naphthyridonecarboxylic acids, respectively.

EP-A-300,311 (Canadian Patent 1333715) discloses a preparation of quinolone-carboxylic acids where a benzoyl chloride is acylated with an aminoacrylic ester, and an amine exchange is carried out with the aroylacrylic ester. The resulting aminoacrylate is cyclized, the resulting ester is hydrolyzed, and the resulting quinolone-carboxylic acid is precipitated out by addition of an acid. The patent reports that yields between 71 and 79% are obtained. The solvents which are given for the for the acylation step include toluene, xylene, cyclohexane, open-chain hydrocarbons, and polar solvents such as dimethyl formamide (DMF) and dimethyl sulphoxide (DMSO). The solvents which are given for the amine-exchange step include the above-mentioned solvents as well as protic polar solvents, e.g., alcohols such as butyl glycol. Suitable solvents for the cyclization steps include only polar solvents such as higher alcohols, amino alcohols, DMF, DMSO, dioxane and N-methylpyrrolidone.

If non-polar to slightly polar solvents such as hydrocarbons are to be employed for the acylation and the amine exchange, a different polar, optionally even protic solvent, such as butyl alcohol, has to be employed for the cyclization. As such, to carry out the entire reaction in one solvent seems possible only in a strongly polar solvent such as DMF and DMSO. In the examples of EP-A 300 311, for instance, the solvent was changed, namely from the non-polar aprotic toluene or cyclohexane for the first solvent and, if appropriate, the second step to the polar, protic butyl glycol for the third and, if appropriate, second step.

The change of solvent leads to considerable expense for the separate removal of two different solvents, for drying the intermediate at whose stage the solvent exchange is carried out and for disposal or regeneration of two different solvents. Further, the yields which can be obtained are still not entirely satisfactory.

According to EP-A 176,846, for reacting a benzoyl halide with an acrylic acid derivative (=acylation), use is made of methylene chloride, chloroform, toluene, tetrahydrofuran or dioxane.

In Liebigs Ann Chem. 1987, 29–37, a dipolar aprotic solvent, for example, DMF, DMSO or N-methylpyrrolidone, is specified for the cyclocondensation of 3-amino-2-benzoylacrylic esters to 4-quinolone-3-carboxylic esters (=cyclization).

Thus, there is a general bias in the art against using a non-polar to slightly polar solvent for the entire reaction sequence.

DESCRIPTION OF THE INVENTION

The invention relates to a process for preparing quinolone- and naphthyridonecarboxylic acids and esters thereof of the formula (I)

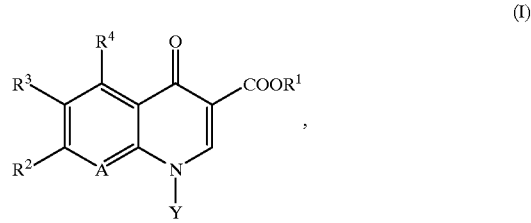

(I)

in which $R^1$ represents hydrogen or $C_1$–$C_4$-alkyl groups;

$R^2$ represents a halogen group;

$R^3$ represents a halogen group;

$R^4$ represents hydrogen, halogen and nitro groups;

Y represents $C_1$–$C_6$-alkyl, 2-fluoroethyl, cyclopropyl, fluorocyclopropyl, isopropyl, 4-fluorophenyl and 2,4-difluorophenyl groups; and A represents nitrogen atoms or C—$R^5$ groups, in which $R^5$ includes hydrogen atoms, methyl groups, methoxy groups, halogen groups, nitro groups or cyano groups, where Y and $R^5$ together may also represent —$CH_2$—$CH_2$—O— or —$CH(CH_3)$—$CH_2$—O—groups, where the terminal $CH_2$— or the $CH(CH_3)$— group is attached to the nitrogen atom.

The process generally includes the steps of a) reacting (acylating), in the presence of a base, a benzoyl chloride or a nicotinoyl chloride of the formula (II)

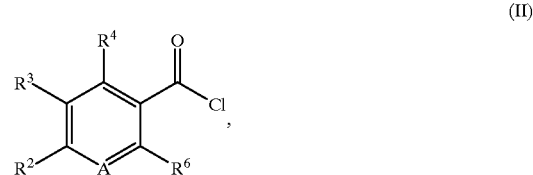

(II)

in which $R^2$, $R^3$, $R^4$ and A are each as defined under formula (I) and $R^6$ represents halogen, with an aminoacrylic ester of the formula (III)

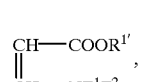

(II)

in which $R^1$ represents a $C_1$–$C_4$-alkyl group; and $Z^1$ and $Z^2$ independently of one another represent a $C_1$–$C_4$-alkyl group, or together with the linking nitrogen atom form a 5- to 6-membered saturated or unsaturated ring which may optionally contain up to two further hetero groups selected from the group consisting of O atoms, S atoms and $SO_2$ groups to produce a (Het)-aroylacrylic ester of the formula (IV)

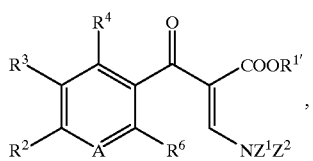

in which

R$^{1'}$ represents a C$_1$–C$_4$-alkyl group and

R$^2$, R$^3$, R$^4$ and A each are as defined in formula (I),

R$^6$ is as defined under formula (II), and

Z$^1$ and Z$^2$ are each as defined in formula (III);

b) subjecting the (Het)-aroylacrylic ester of the formula (IV) to an amine exchange with an amine of the formula (V)

 (V), in which Y is as defined in formula (I), to produce a (Het)-aroylacrylic ester of the formula (VI)

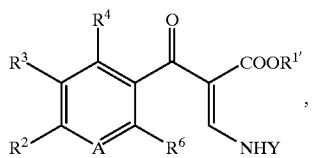

in which R$^{1'}$ represents a C$_1$–C$_4$-alkyl group and

R$^2$, R$^3$, R$^4$, Y and A are each as defined under formula (I) and

R$^6$ is as defined under formula (II);

c) cyclizing the (Het)-aroylacrylic ester of the formula (VI) in the presence of a base to produce a quinolone or naphthyridone ester of the formula (I) in which R$^1$ represents a C$_1$–C$_4$ alkyl group;

d) if a quinolone or napthyridonecarboxylic acid of the formula (I) is to be prepared in which R$^1$ represents hydrogen, the ester which is present after step c) is hydrolyzed and the acid of the formula (I) in which R$^1$ represents hydrogen is isolated after addition of an acid;

where the intermediates of the formulae (IV) and (VI) are not isolated and steps a) to c) are carried out in the presence of the same non-polar to slightly polar solvent. Although the same non-polar to slightly polar solvent is used in steps a) to c), it is understood that other solvents can be present in the system.

The symbols used in the formulae (I) to (VI) preferably refer to the following:

if

R$^1$ represents a C$_1$–C$_4$-alkyl group, e.g., methyl or ethyl group,

R$^2$ represents chlorine or fluorine groups,

R$^3$ represents fluorine groups,

R$^4$ represents hydrogen, chlorine, fluorine or nitro groups,

R$^6$ represents fluorine or chlorine groups,

A represents C—R$^5$ in which R$^5$ is selected from groups such as hydrogen, methyl, methoxy, halogen or cyano, or N groups.

Y represents ethyl, cyclopropyl, fluorocyclopropyl, 2,4-difluorophenyl or together with R$^5$—CH(CH$_3$)—CH$_2$—O—, Z$^1$ and Z$^2$ each represents methyl or ethyl groups.

Suitable reaction temperatures for step a) are generally in the range from 25 to 120° C. Preference is given to carrying out the reaction at from 30 to 80° C. Suitable bases for step a) are, for example, tertiary amines, like those of the formulae

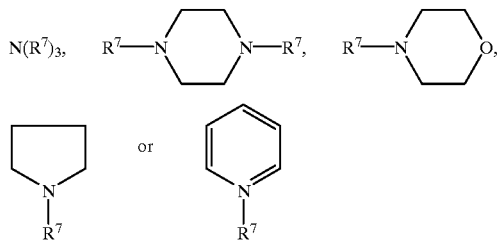

in which R$^7$ represents a C$_1$–C$_{14}$-alkyl group or a benzyl group.

If a plurality of R$^7$ groups is present in a molecule, these groups may be identical or different. R$^7$ preferably represents a C$_1$–C$_4$-alkyl group. A particularly preferred tertiary amine is triethylamine.

In step a), generally at least one equivalent of base is employed per mole of the acyl chloride of the formula (II). This amount is preferably from 1 to 2 equivalents. Greater amounts are not critical, but uneconomical.

Hydrochloride of the base employed which precipitates out during the reaction can, if required, be removed mechanically, e.g., by filtration, or by extraction with water. Preferably, this hydrochloride is not separated off.

Suitable reaction temperatures for step b) are, for example, in the range from 5 to 100° C. Preference is given to carrying out the reaction at from 10 to 80° C. Preferred amines of the formula (V) are ethylamine, cyclopropylamine, 2, 4-difluoroaniline, aminopropanol and fluorocyclopropylamine.

In step b) in general at least one equivalent of amine is employed per mole of ester of the formula (IV). This amount is preferably from 1 to 1.3 equivalents. Greater amounts are not critical, but uneconomical.

The liberated dialkylamine, preferably dimethyl- or diethylamine, is preferably removed from the reaction mixture. This may be done, for example by adding an equivalent of acid and mechanical removal, by filtration, or by extraction with water. If appropriate, the hydrochloride produced in step a) can also be separated off here. The liberated dialkylamine can also be removed from the reaction mixture by distillative removal at a suitable temperature, e.g., low temperatures.

Suitable reaction temperatures for step c) are, for example, in the range from 50 to 200° C. The respective optimum reaction temperature depends on the substitution pattern and can easily be determined by routine preliminary experiments. Suitable bases for step c) include, for example, potassium carbonate, sodium carbonate, sodium hydride and sodium tert-butoxide. Preference is given to potassium carbonate. Based on 1 mol of the compound of the formula (VI), it is possible to employ, for example, from 1 to 4 molar equivalents of the base. This amount is preferably from 1.1 to 1.5 molar equivalents. When using potassium carbonate or sodium carbonate, it is advantageous to remove the water of reaction which is liberated, for example using a water separator. Step c) can, if appropriate, be carried out in the presence of a phase-transfer catalyst. Suitable phase-transfer catalysts include, for example, tetraalkyl-ammonium halides.

The ester of the formula (I) where $R^1=C_1-C_4$-alkyl can be isolated, for example, as follows. Initially, a fraction of the solvent is distilled off, e.g., from 40 to 60% by weight. Water is then added, upon which in general the ester begins to precipitate out. The remaining solvent is then distilled off and the ester is then separated off, for example, by filtration, washed with an alcohol, e.g., a $C_1-C_4$-alkyl alcohol, and subsequently dried under reduced pressure.

The ester hydrolysis for preparing acids of the formula (I) where $R^1$=hydrogen from esters of the formula (I) where $R^1=C_1-C_4$-alkyl can be carried out by customary methods in an acidic or in an alkali medium. If the esters in question are base-sensitive esters of the formula (I), preference is, of course, given to hydrolyzing the esters in an acidic medium.

For separating off and isolating acids of the formula (I), it is possible to add, for example, acetic acid, sulphuric acid or hydrochloric acid. The precipitated acid can be separated off, for example, by filtration.

It is an essential feature of the process according to the invention that the intermediates of the formulae (IV) and (VI) obtained after carrying out steps a) and b) are not isolated. It is another essential feature of the process according to the invention that steps a) to c) are carried out without solvent exchange in the polar solvent or slightly polar solvent, e.g., the same non-polar to slightly polar solvent.

Suitable solvents include but are not limited to alkylbenzenes, particularly those containing from 1 to 3 $C_1-C_4$-alkyl groups per molecule; halogenobenzenes, particularly those containing from 1 to 2 halogen atoms, preferably chlorine atoms, per molecule; halogenoalkylbenzenes, in particular those containing from 1 to 2 halogen atoms preferably chlorine atoms, and from 1 to 2 $C_1-C_4$-alkyl groups per molecule; alicyclic hydrocarbons, particularly those which contain from 5 to 7 ring carbon atoms and which are optionally substituted with from 1 to 2 $C_1-C_4$-alkyl groups, open-chain, saturated or unsaturated hydrocarbons, in particular, those which are straight-chain or branched and contain from 5 to 18 carbon atoms, and any mixtures of such solvents.

In selecting solvents, care should be taken to choose those solvents whose boiling point at atmospheric pressure is above the intended reaction temperature or, in the case of reaction temperatures above the boiling point of the intended solvent at atmospheric pressure, to use pressure-proofed, closed apparatuses. If the boiling point of the solvent at atmospheric pressure exceeds the intended reaction temperature substantially, it is also possible to operate under reduced pressure.

Particular examples of solvents also include toluene, xylenes, mesitylene, ethylbenzene, diethylbenzenes, isopropylbenzene, chlorobenzene, dichlorobenzenes, chlorotoluenes, cyclohexane and hydrocarbon mixtures which contain at least 80% by weight of one or more straight-chain or branched $C_6$- to $C_{12}$-hydrocarbons. Preferred solvents are toluene, xylenes, mesitylene, isopropylbenzene, chlorobenzene and dichlorobenzenes.

It is possible to use, for example, from 300 to 1000 ml of solvent per mole of acyl chloride of the formula (II). This amount is preferably from 400 to 800 ml. Greater amounts of solvent are not critical, but uneconomical.

The process according to the invention has the advantages that three reaction steps can be carried out without isolating intermediates and without changing the solvent, and that higher yields than in the prior art are obtained. The yields which can be obtained are above 80% of theory, frequently above 85% of theory. This means that the process according to the invention can be carried out in a technically simple manner and particularly effectively, since the expenditure for the removal and disposal or regeneration of a second solvent and for the isolation and drying of intermediates is not incurred, and it is still possible to obtain higher yields than hitherto. Another advantage is that the process does not utilize any appreciable amount, (preferably none) polar solvents such as dimethyl formamide (DMF) and dimethyl sulphoxide (DMSO). These obtainable advantages are extremely surprising, because hitherto the use of polar solvents had been thought to be central, at least for the cyclization reaction (step c).

Particularly preferred compounds which can be prepared by the process according to the invention from the corresponding compounds of the formulae (II), (III) and (V) are the following: 1-cyclopropyl-7-chloro-6-fluoro- 1,4-dihydro-4-oxo-3-quinoline-carboxylic acid; ethyl 1-cyclopropyl-6,7,8-trifluoro-1,4-dihydro-4-oxo-3-quinoline-carboxylate; ethyl 1-cyclopropyl-6,7-difluoro-1,4-dihydro-4-oxo-3-quinoline-carboxylate; ethyl 1-cyclopropyl-6,7-difluoro-8-methoxy-1,4-dihydro-4-oxo-3-quinoline-carboxylate; ethyl 1-cyclopropyl-6,7-difluoro-8-cyano-1,4-dihydro-4-oxo-3-quinolinecarboxylate; ethyl 1-(2-fluoro)cyclopropyl-6,7-difluoro-1,4-dihydro-4-oxo-3-quinoline-carboxylate; ethyl 1-cyclopropyl-8-chloro-6,7-difluoro-1,4-dihydro-4-oxo-3-quinoline-carboxylate; ethyl 1-ethyl-6,7,8-trifluoro-1,4-dihydro-4-oxo-3-quinoline-carboxylate; ethyl 7-chloro-1-(2,4-difluoro-phenyl)-6-fluoro-1,4-dihydro-4-oxo-1,8-naphthyridone-3-carboxylate; ethyl 7-chloro-1-cyclopropyl-6-fluoro-1,4-dihydro-4-oxo-1,8-naphthyridone-3-carboxylate; ethyl 1-cyclopropyl-7-chloro-6-fluoro-1,4-dihydro-4-oxo-3-quinoline-carboxylate and ethyl 9,10-difluoro-2,3-dihydro-3-methyl-7-oxo-7H-pyrido(1,2,3-de)(1,4)benzoxazine-6-carboxylate.

A specific aspect of the present invention is a process for cyclizing a (Het)-aroylacrylic ester of the formula (VI)

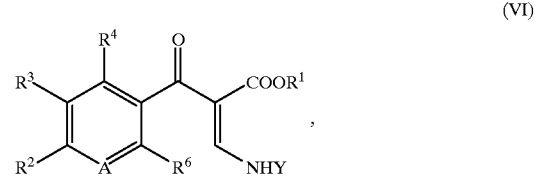

(VI)

wherein
$R^{1'}$ represents a $C_1-C_4$-alkyl group,
$R^2$ represents a halogen group,
$R^3$ represents a halogen group,
$R^4$ represents hydrogen, halogen or nitro groups,
$R^6$ represents a halogen group,
Y represents $C_1-C_6$-alkyl, 2-fluoroethyl, cyclopropyl, fluorocyclopropyl, isopropyl, 4-fluorophenyl or 2,4-difluorophenyl groups and
A represents nitrogen or C—$R^5$ groups where $R^5$ represents hydrogen, methyl, methoxy, halogen, nitro or cyano groups, and
where Y and $R^5$ together may also represent —CH$_2$—CH$_2$—O— or
—CH(CH$_3$)—CH$_2$—O—, where the terminal CH$_2$— or the CH(CH$_3$)— group is attached to the nitrogen atom, in the presence of a base, forming an ester of the formula (I)

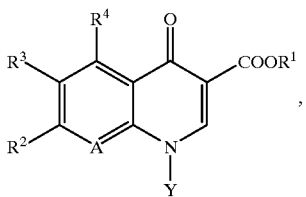

(I)

in which the symbols used are each as defined above in formula (VI), characterized in that the process is carried out in the presence of a non-polar to slightly polar solvent, e.g., the same non-polar to slightly polar solvent. This process is described above in more detail. Preferred non-polar to slightly polar solvents include alkylbenzenes, halogenobenzenes, halogenoalkylbenzenes, alicyclic hydrocarbons, open-chain hydrocarbons and any mixtures of such solvents.

The invention is further illustrated but is not intended to be limited by the following examples in which all parts and percentages are by weight unless otherwise specified.

EXAMPLES

Example 1

At 70° C., 160 g of 2,4-dichloro-5-fluorobenzoyl chloride were added dropwise over a period of 50 minutes to a solution of 380 g of dichlorobenzene (mixture of isomers), 110 g of ethyl N,N-dimethylaminoacrylate and 77 g of triethylamine. The mixture was subsequently stirred at 70° C. for 2 hours and cooled to room temperature. At room temperature, 51 g of acetic acid were added and the mixture was again heated to 70° C. At 70° C., 45 g of cyclopropylamine were then added dropwise, the reaction mixture was subsequently admixed with 100 ml of water and the organic phase that formed was separated off. The organic phase was metered into a mixture of 59 g of potassium carbonate and 190 g of dichlorobenzene (mixture of isomers) at from 180 to 184° C. The water of reaction which was liberated was separated off via a water separator. After all the water had been separated off, the mixture was cooled to 80° C. and, at a pressure of 40 mbar, 340 ml of dichlorobenzene were distilled off. 80 g of 35% strength aqueous sodium hydroxide solution and 350 g of water were then added, and the remaining dichlorobenzene was distilled off. After addition of 180 g of acetic acid and 100 g of water, the product was filtered off with suction and the isolated solid was washed 3 times with 150 ml of water each time and 3 times with 200 ml of isopropanol each time. Drying under reduced pressure at 60° C. gave 173 g of 1-cyclopropyl-7-chloro-6-fluoro-1,4-dihydro-4-oxo-3-quinoline-carboxylic acid. This corresponds to a yield of 87% of theory.

Example 2

A mixture of 380 g of xylene (mixture of isomers), 110 g of ethyl N,N-dimethylaminoacrylate and 77.4 g of triethylamine was initially charged, and 160 g of 2,4-dichloro-5-fluorobenzoyl chloride were added dropwise at 70° C. over a period of 60 minutes. The mixture was subsequently stirred at 70° C. for 2 hours and cooled to room temperature. At room temperature, 51 g of acetic acid were then added, and the mixture was again heated to 70° C. At 70° C., 45 g of cyclopropylamine were then added dropwise. 100 ml of water were added to the reaction mixture which was stirred for 15 minutes, and the organic phase that formed was separated off. The organic phase was metered into a mixture of 89 g of potassium carbonate and 190 g of xylene (mixture of isomers) at from 140 to 142° C. The water of reaction that was liberated was separated off via a water separator. After all the water had been separated off, the mixture was cooled to 80° C. and, at a pressure of 40 mbar, xylene was distilled off. 80 g of 45% strength aqueous sodium hydroxide solution and 350 g of water were then added, and the remaining xylene was distilled off. After addition of 180 g of acetic acid and 100 g of water, the product was filtered off with suction and the solid was washed 3 times with 150 ml of water each time and 3 times with 200 ml of isopropanol each time. Drying under reduced pressure at 60° C. gave 170 g of 1-cyclopropyl-7-chloro-6-fluoro-1,4-dihydro-4-oxo-3-quinoline-carboxylic acid. This corresponds to a yield of 86% of theory.

Example 3

380 g of chlorobenzene, 110 g of ethyl N,N-dimethylaminoacrylate and 77.4 g of triethylamine were initially charged, and 160 g of 2,4-dichloro-5-fluorobenzoyl chloride were added dropwise at 70° C. over a period of 60 minutes. The mixture was subsequently stirred at 70° C. for 2 hours and then cooled to room temperature. 51 g of acetic acid were then added at room temperature, and the mixture was again heated to 70° C. At 70° C., 45 g of cyclopropylamine were then added dropwise. 100 ml of water were added to the reaction mixture which was stirred for 15 minutes, and the organic phase that formed was separated off. The aqueous phase was extracted with 50 ml of chlorobenzene and the combined organic phases were metered into a mixture of 119 g of potassium carbonate, 1 g of tributylammonium bromide and 190 g of chlorobenzene, at 131° C. The water of reaction that was liberated was separated off via a water separator. After all the water had been separated off, the mixture was cooled to 20° C. and the precipitated solid was filtered off with suction using a nutsche filter.

The solid was then washed 3 times with 200 ml of isopropanol each time. Drying under reduced pressure at 60° C. gave 186 g of ethyl 1-cyclopropyl-7-chloro-6-fluoro-1,4-dihydro-4-oxo-3-quinoline-carboxylate. This corresponds to a yield of 86% of theory.

Example 4

At 45° C., 280 g of 2,3,4,5-tetrafluorobenzoyl chloride were added dropwise over a period of 60 minutes to a solution of 270 g of toluene, 189.8 g of ethyl N,N-dimethylaminoacrylate and 144.2 g of triethylamine. The mixture was subsequently stirred at 50° C. for 1 hour and then cooled to room temperature. At room temperature, 95.2 g of acetic acid were then added, and 75.2 g of cyclopropylamine were then added dropwise at from 20 to 30° C. 200 ml of water were then added to the reaction mixture, and the organic phase that formed was separated off. The aqueous phase was extracted with 82 g of toluene and the combined organic phases were metered into a mixture of 110 g of potassium carbonate and 404 g of toluene, at 111° C. The water of reaction that was liberated was separated off via a water separator. After all the water had been separated off, the mixture was cooled to 60° C. and 1280 g of water were added. At a temperature of 40° C. and a pressure of 100 mbar, the toluene was distilled off. The suspension was cooled to 20° C. and filtered off with suction using a nutsche filter. The solid was then washed 3 times with 200ml of water each time and 3 times with 250 ml of isopropanol each time and subsequently dried at 50° C. under reduced pressure. This gave 374 g of ethyl 1-cyclopropyl-6,7,8-trifluoro-1,4-dihydro-4-oxo-3-quinoline-carboxylate. This corresponds to a yield of 91% of theory.

Example 5

At 45° C., 140 g of 2,3,4,5-tetrafluorobenzoyl chloride were added dropwise over a period of 60 minutes to a solution of 202 g of toluene, 94.9 g of ethyl N,N-dimethylaminoacrylate and 72.1 g of triethylamine. The mixture was subsequently stirred at 43° C. for 1 hour and then cooled to room temperature. 37.6 g of cyclopropylamine were then added dropwise at from 20 to 30° C., and the mixture was stirred for 1 hour. The dimethyl-amine was subsequently distilled off at a pressure of 80 mbar. 100 ml of water were added to the reaction mixture, and the organic phase that formed was separated off. The aqueous phase was extracted with 41 g of toluene and the combined organic phases were metered into a mixture of 55 g of potassium carbonate and 202 g of toluene, at 110° C. The water of reaction that was liberated was separated off via a water separator. After all the water had been separated off, the mixture was cooled to 60° C. and 640 g of water were added. At a temperature of 40° C. and a pressure of 100 mbar, the toluene was distilled off. The suspension was cooled to 20° C. and filtered off with suction using a nutsche filter. The resulting solid was washed 3 times with 150 ml of water each time and 3 times with 150 ml of isopropanol each time and subsequently dried under reduced pressure at 50° C. This gave 172 g of ethyl 1-cyclopropyl-6,7,8-trifluoro-1,4-dihydro-4-oxo-3-quinoline-carboxylate. This corresponds to a yield of 84% of theory.

Example 6

Example 2 was repeated, but isopropylbenzene was used instead of xylene, and the cyclization was carried out at from 156 to 158° C. Drying under reduced pressure at 60° C. gave 177 g of 1-cyclopropyl -7-chloro -6-fluoro-1,4-dihydro-4-oxo-3-quinoline-carboxylic acid. This corresponds to a yield of 89% of theory.

Example 7

Example 2 was repeated, but mesitylene was used instead of xylene, and the cyclization was carried out at from 166 to 168° C. Drying under reduced pressure at 60° C. gave 174 g of 1-cyclopropyl-7-chloro-6-fluoro-1,4-dihydro-4-oxo-3-quinoline-carboxylic acid. This corresponds to a yield of 88% of theory.

Example 8

272 g of toluene, 111 g of ethyl N,N-dimethylaminoacrylate and 85 g of triethylamine were initially charged, and 156 g of 2,4,5-trifluorobenzoyl chloride were added dropwise at from 50 to 55° C. over a period of 60 minutes. The mixture was subsequently stirred at 55° C. for 2 hours and then cooled to room temperature. 56 g of acetic acid were then added, and 48.6 g of cyclopropylamine were added dropwise at from 20 to 30° C. 250 ml of water were then added to the reaction mixture which was stirred for 15 minutes, and the organic phase was separated off. The organic phase was metered into a mixture of 65 g of potassium carbonate and 240 g of toluene, at 110° C. The water of reaction that was liberated was separated off via a water separator. After all the water had been separated off, the mixture was cooled to 30° C., and 500 ml of water were added. At a pressure of from 120 to 180 mbar, the toluene was distilled off. The mixture was subsequently cooled to 20° C. and the product was filtered off with suction. The isolated solid was washed three times with 100 ml of water each time and three times with 100 ml of isopropanol each time. Drying under reduced pressure at 50° C. gave 206 g of ethyl 1-cyclopropyl-6,7-difluoro-1,4-dihydro-4-oxo-3-quinoline-carboxylate. This corresponds to a yield of 88% of theory.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing quinolone- and naphthyridon-ecarboxylic acids and esters thereof of the formula (I).

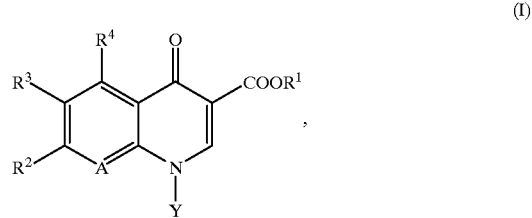

wherein
$R^1$ comprises a component selected from the group consisting of hydrogen and $C_1$–$C_4$-alkyl groups;
$R^2$ comprises a halogen group;
$R^3$ comprises a halogen group;
$R^4$ comprises a component selected from the group consisting of hydrogen, halogen and nitro groups;
Y comprises a component selected from the group consisting of $C_1$–$C_6$ alkyl, 2-fluoroethyl, cyclopropyl, fluorocyclopropyl, isopropyl, 4-fluorophenyl and 2,4-difluorophenyl groups; and
A comprises a component selected from the group consisting of nitrogen, C—$R^6$ groups, wherein $R^5$ is selected from the group consisting of hydrogen, methyl, methoxy, halogen, nitro and cyano;
the process comprising the steps of:
  a) acylating, in the presence of a base,
    (a) a benzoyl chloride or a nicotinoyl chloride of the formula (II)

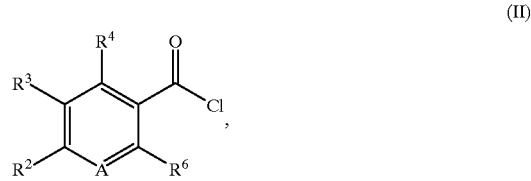

wherein $R^2$, $R^3$, $R^4$ and A are each as defined under formula (I) and $R^6$ comprises halogen;
with (b) an aminoacrylic ester of the formula (III)

wherein $R^{1'}$ comprises a component selected from the group consisting of $C_1$–$C_4$-alkyl groups; and $Z^1$ and $Z^2$ independently of one another each comprise a component selected from the group consisting of $C_1$–$C_4$-alkyl groups, $C_1$–$C_4$-alkyl groups together with a linking nitrogen atom forming a 5- to 6-membered saturated or unsaturated rings, said 5- to 6-membered saturated or unsaturated rings containing up to two further hetero groups selected from the group consisting of O and S atoms and a $SO_2$ group;

to produce a (het)-aroylacrylic ester of the formula (IV)

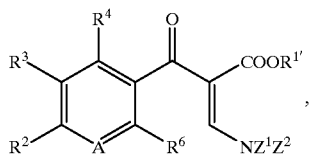

(IV)

wherein $R^{1'}$ comprises a component selected from the group consisting of $C_1$–$C_4$-alkyl groups and $R^2$, $R^3$, $R^4$ and A each are as defined in formula (I), $R^6$ is as defined under formula (II), and $Z^1$ and $Z^2$ are each as defined in formula (III);

b) subjecting the (het)-aroylacrylic ester of the formula (IV) to an amine exchange with an amine of the formula (V)

 (V), wherein Y is as defined in formula (I), to produce a (het)-aroylacrylic ester of the formula (VI)

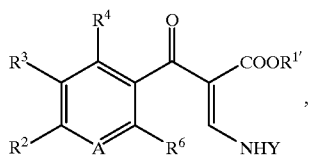

(VI)

wherein
$R^{1'}$ comprises a component selected from the group consisting of $C_1$–$C_4$, alkyl groups and $R^2$, $R^3$, $R^4$, Y and A are each as defined under formula (I) and
$R^6$ is as defined under formula (II), c) cyclizing the (het)-aroylacrylic ester of the formula (VI) in the presence of the base without utilizing a polar solvent selected from the group consisting of dimethylformamide, dimethyl sulfoxide, tetramethylene sulfone, and N-methylpyrrolldone, to produce a quinolone or naphthyridone ester of the formula (I) wherein $R^1$ comprises a component selected from the group consisting of $C_1$–$C_4$ alkyl groups;

wherein the intermediates of the formulae (IV) and (VI) are not isolated and steps a) to c) are carried out in the same non-polar to slightly polar solvent.

2. The process of claim 1, wherein the intermediates of the formulae (IV) and (VI) obtained after carrying out steps a) and b) are not isolated.

3. The process of claim 1, wherein the ester which is present after step c) is hydrolyzed to form an acid of the formula (I), wherein $R^1$ comprises hydrogen, and the acid of formula (I) is isolated after addition of an acid.

4. The process of claim 1, wherein the non-polar solvent or slightly polar solvent used comprises a solvent selected from the group of solvents consisting of alkylbenzene, halogenobenzene, halogenoalkylbenzene, alicyclic hydrocarbon, open-chain hydrocarbon, and mixtures thereof.

5. The process of claim 1, wherein the non-polar solvent or slightly polar solvent used comprises a solvent selected from the group consisting of toluene, xylene, mesitylene, isopropylbenzene, chlorobenzene and dichlorobenzene.

6. The process of claim 1, wherein the non-polar solvent or slightly polar solvent is employed in an amount ranging from 300 to 1000 ml per mole of acyl chloride of the formula (II).

7. The process of claim 1, wherein:
$R^1$ comprises a $C_1$–$C_4$ alkyl group selected from group consisting of methyl and ethyl groups,
$R^2$ comprises chlorine or fluorine,
$R^3$ comprises fluorine,
$R^4$ comprises a component selected from the group consisting of hydrogen, chlorine, fluorine and nitro groups,
$R^6$ comprises fluorine or chlorine,
A comprises C—$R^5$, wherein $R^5$ comprises a group selected from the group consisting of hydrogen, methyl, methoxy, halogen, cyano and N groups,
Y comprises a component selected from the group consisting of ethyl, cyclopropyl, fluorocyclopropyl, 2,4-difluorophenyl, $R^5$, CH($CH_3$)—$CH_2$—O— groups and
$Z^1$ and $Z^2$ comprise a component selected from the group consisting of methyl and ethyl groups.

8. The process of claim 1, wherein step a) is carried out at a temperature ranging from 25 to 120° C., step b) is carried out at a temperature ranging from 5 to 100° C.

9. The process of claim 1, wherein
(1) the base used in step a) comprises a tertiary amine,
(2) the amine used in step b) comprises an amine component selected from the group consisting of ethylamine, cyclopropylamine, 2,4-difluoroaniline, aminopropanol and fluorocyclopropylamine and
(3) the base used in step c) comprises a component selected from the group consisting of potassium carbonate, sodium carbonate, sodium hydride and sodium tert-butoxide.

10. The process of claim 1, wherein the quinolone- and naphthyridonecarboxylic acids and esters thereof of the formula (I) are obtained in a yield that is more than 80%.

11. The process of claim 1, wherein the quinolone- and naphthyridonecarboxylic acids and esters thereof of the formula (I) are obtained in a yield that is more than 85%.

12. The process of claim 1, wherein Y and $R^5$ together represent —$CH_2$—$CH_2$—O— or —CH($CH_3$)—$CH_2$—O—, where the terminal $CH_2$— or the CH($CH_3$)— group is attached to the nitrogen atom.

13. A process for making an ester of the formula (I)

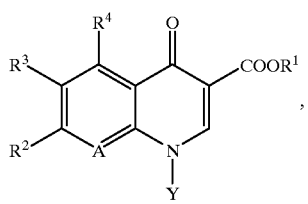

(I)

wherein $R^1$, $R^2$, $R^3$, $R^4$ A and Y are each as defined above in formula (VI), wherein the process comprises cyclizing a (het)-aroylacrylic ester of the formula (VI) in the presence of a non-polar to slightly polar solvent, without utilizing a polar solvent selected from the group consisting of dimethylformamide, dimethyl sulfoxide, tetramethylene sulfone and N-methylpyrrolidone;

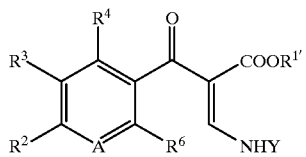

(VI)

wherein
$R^1$ comprises $C_1$–$C_4$-alkyl,
$R^2$ comprises halogen,
$R^3$ comprises halogen,
$R^4$ comprises hydrogen, halogen or nitro,
$R^6$ comprises halogen,
Y comprises $C_1$–$C_6$-alkyl, 2-fluoroethyl, cyclopropyl, fluorocyclopropyl, isopropyl, 4-fluorophenyl or 2,4-difluorophenyl and
A comprises nitrogen or C—$R^5$ where $R^5$ is hydrogen, methyl, methoxy, halogen, nitro or cyano.

14. Process according to claim 13, wherein the solvent used comprises a component selected from the group consisting of alkylbenzene solvents, halogenobenzene solvents, halogenoalkylbenzene solvents, alicyclic hydrocarbon solvents, open-chain hydrocarbon solvents, and mixtures of these solvents.

15. The process of claim 13, wherein Y and $R^5$ together represent —$CH_2$—$CH_2$—O— or —$CH(CH_3)$—$CH_2$—O—, wherein the terminal $CH_2$— or the $CH(CH_3)$— group is attached to the nitrogen atom.

* * * * *